United States Patent [19]

Baillie et al.

[11] Patent Number: 4,916,079
[45] Date of Patent: Apr. 10, 1990

[54] METHOD AND SYSTEM FOR DETERMINING THE CONCENTRATION OF A GAS IN A LIQUID

[75] Inventors: Lloyd A. Baillie; Frank H. Hsu, both of Plano, Tex.

[73] Assignee: Atlantic Richfield Company, Los Angeles, Calif.

[21] Appl. No.: 193,965

[22] Filed: May 13, 1988

[51] Int. Cl.$^4$ ............................................. G01N 33/00
[52] U.S. Cl. .................................. 436/174; 422/68.1; 422/81; 436/52
[58] Field of Search ................... 436/174, 52; 422/68, 422/81

[56] References Cited

U.S. PATENT DOCUMENTS

| 3,147,082 | 9/1964 | Thompson | 23/230 |
| 3,920,396 | 11/1975 | Schuy | 23/230 B |
| 3,973,915 | 8/1976 | Raffaele et al. | 23/259 |
| 4,119,406 | 10/1978 | Clemens | 422/81 |
| 4,253,845 | 3/1981 | Smernoff | 23/230 B |
| 4,294,800 | 10/1981 | Tavlarides et al. | 422/68 |
| 4,424,276 | 1/1984 | Clark et al. | 436/50 |
| 4,600,697 | 7/1986 | Smernoff | 436/174 |

Primary Examiner—Michael S. Marcus
Assistant Examiner—Thalia P. Vassilatos
Attorney, Agent, or Firm—Michael E. Martin

[57] ABSTRACT

The concentration of a gas such as hydrogen sulfide in a liquid such as crude oil or other hydrocarbon liquid is measured by conducting a flowstream of the liquid through a jet or eductor type pump for mixing a recirculating vapor stream with the liquid, separating the liquid and the vapor stream in a separator to provide equilibrium conditions between the vapor and the liquid and withdrawing the vapor flowstream for recirculation and remixing with the liquid flowstream while measuring the concentration of the gas in the vapor flowstream. A known flow rate of the gas is added to the combined liquid and recirculating vapor flowstream and the incremental change in concentration of the gas in the recirculating vapor flowstream is measured to determine the concentration of the gas in the liquid flowstream initially. The jet type pump utilizes the liquid flowstream and is in communication with a separator chamber, preferably at atmospheric pressure, for separating liquid from the equilibrium vapor flowstream and recirulating the vapor flowstream through a nonconsumptive concentration detector for the gas. The quantity of gas added to the system is conducted to the pump for mixing with the liquid flowstream by way of a bubble counter type flow measuring device.

16 Claims, 1 Drawing Sheet

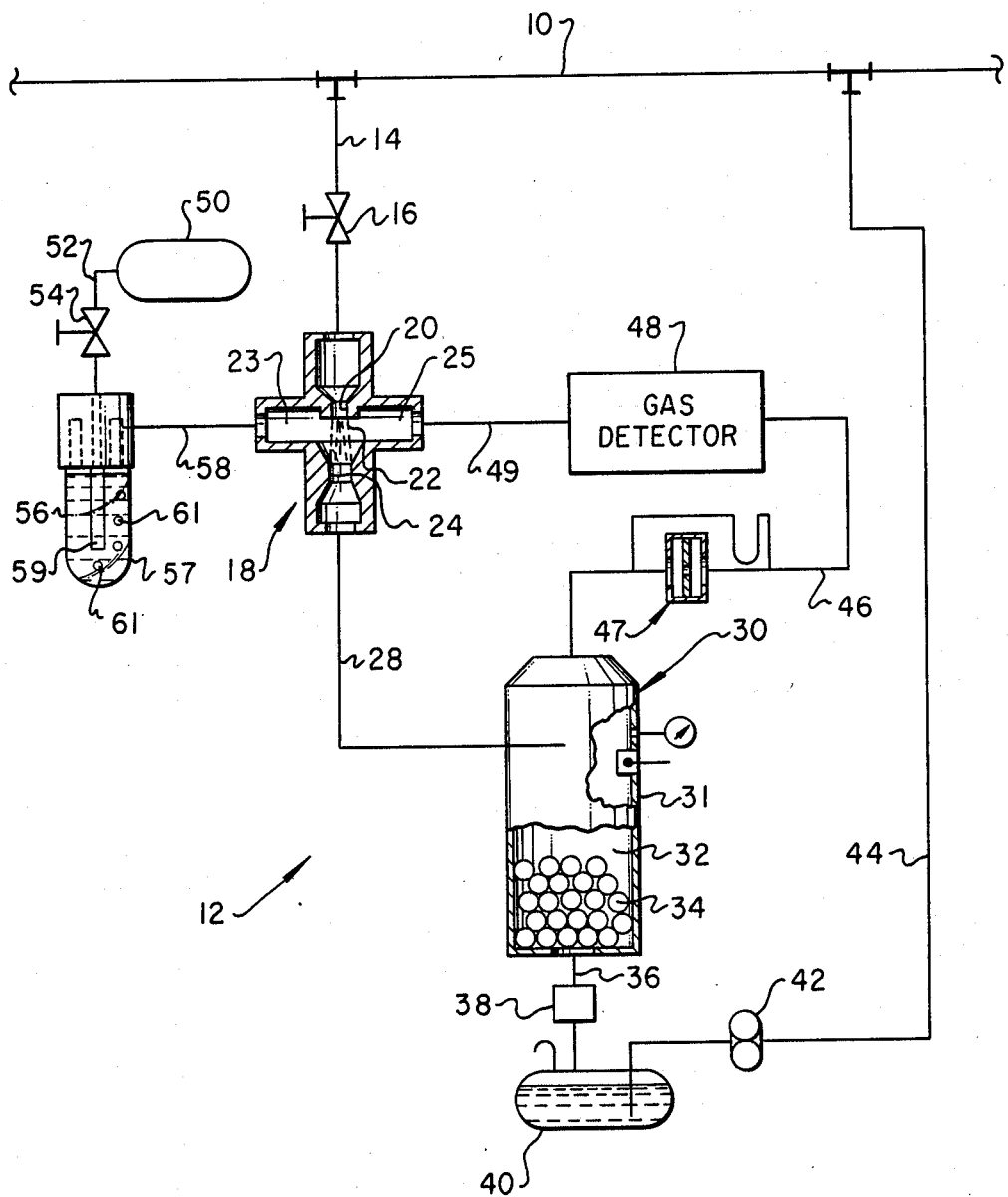

METHOD AND SYSTEM FOR DETERMINING THE CONCENTRATION OF A GAS IN A LIQUID

BACKGROUND OF THE INVENTION

1. Field of the Invention

The present invention pertains to a system and method for determining the concentration of a fluid such as hydrogen sulfide in a liquid hydrocarbon by measuring the indicated incremental gas phase concentration after adding a known quantity of the fluid to be measured to a liquid flowstream which is in equilibrium with a vapor flowstream being measured.

2. Background

The concentration of one fluid in vapor form which is in equilibrium with a liquid such as a liquid hydrocarbon depends on an equilibrium constant which is a function of the temperature and the composition of the liquid. For example, in determining the concentration of hydrogen sulfide in a hydrocarbon flowstream there are various types of measuring devices which measure the concentration of the hydrogen sulfide in a vapor flowstream which is in equilibrium with a quantity of liquid hydrocarbon. One type of device which is known as an MOS detector produces an electrical signal which is determined by the competitive adsorption of oxygen and hydrogen sulfide when exposed to a semiconductor. Accordingly, the signal response of this device depends on the oxygen concentration as well as the hydrogen sulfide concentration in the vapor. Other types of hydrogen sulfide concentration detectors are known, such as a type which produces a chemical change in a tape which is exposed to the vapor stream and a photoelectric device monitors the change in color of the portion of the tape which has been exposed to the vapor stream. Although this type of detector does not require the presence of oxygen in the vapor stream, it is mechanically complicated.

It has been determined that there is a need for a mechanically uncomplicated and reliable system and method for determining the concentration of a fluid in a continuous stream of another fluid which does not rely on the competitive concentrations of different substances in the fluid flowstream and which can accurately determine the concentration of a fluid in a liquid flowstream based on the indicated concentration of the fluid in a vapor flowstream which is in equilibrium with the liquid flowstream. It is to this end that the present invention has been developed.

SUMMARY OF THE INVENTION

The present invention provides an improved system and method for measuring the concentration of one fluid in another, particularly the concentration of a substance such as hydrogen sulfide in a liquid hydrocarbon flowstream.

In accordance with one aspect of the present invention the concentration of a substance such as the hydrogen sulfide in a liquid hydrocarbon is determined by producing a recirculating stream of vapor which is in equilibrium with a flowing stream of liquid, measuring the indicated concentration of the fluid desired to be known in the vapor flowstream, adding a known quantity of the flow whose concentration is to be measured to the vapor flowstream and measuring the incremental change in concentration in the vapor flowstream to determine the actual concentration of the fluid in the liquid flowstream.

The present invention further provides a unique system for measuring the concentration of one substance in a fluid form in the presence of another substance in fluid form, such as the concentration of a contaminant in a liquid hydrocarbon flowstream. The improved system includes a conduit having a pump means therein for mixing a recirculating vapor flowstream with a sample of the liquid flowstream to be measured and to promote placing the recirculating flowstream in equilibrium with a liquid flowstream, a separator for separating vapor from the liquid flowstream, means for adding an incremental, known quantity of the substance whose concentration in the liquid flowstream is to be determined to the vapor-liquid equilibrium flowstream and means for measuring the indicated change in the concentration of the substance to be measured in the recirculating vapor flowstream. The present invention also provides a system which advantageously utilizes an eductor or jet-type pump for mixing the recirculating vapor flowstream and the added incremental amount of fluid whose concentration is to be measured to the liquid flowstream to facilitate placing the vapor flowstream and liquid flowstream in equilibrium. The system further advantageously utilizes a centrifugal separator for separating the liquid from the recirculating vapor flowstream and a detector interposed in the recirculating vapor flowstream for measuring the concentration n the vapor flowstream of the desired substance.

The present invention provides a unique, uncomplicated system and method for measuring the concentration of a substance, such as hydrogen sulfide which is dissolvable in a liquid hydrocarbon, based on the indicated incremental change in the concentration of the substance in a vapor which is in equilibrium with the liquid. The system and method may be utilized to measure a continuous stream of liquid so that substantially constant monitoring of the concentration of one fluid in another fluid may be readily determined.

Those skilled in the art will recognize the abovedescribed advantages and superior features of the invention as well as other important aspects thereof upon reading the detailed description which follows in conjunction with the drawing.

BRIEF DESCRIPTION OF THE DRAWING

The drawing FIGURE comprises a schematic diagram of a preferred embodiment of the system of the present invention.

DESCRIPTION OF A PREFERRED EMBODIMENT

In the description which follows, like parts and elements are marked throughout the specification and drawing with the same reference numerals, respectively. None of the elements of the drawings are drawn to scale and certain elements are shown in schematic form in the interest of clarity of conciseness.

Referring to the drawing, a liquid transmission conduit is indicated by the numeral 10 which may, for example, be a crude oil transmission pipeline. One relatively important measurement of crude oil flow upon production from subterranean wells is the concentration of hydrogen sulfide in the oil flowstream. In accordance with the present invention, an improved system for measuring the concentration of hydrogen sulfide in a crude oil or other liquid hydrocarbon flowstream is provided and generally indicated by the numeral 12. The system 12 includes a sample withdrawal conduit 14 connected to the liquid transmission line and having a flow control valve 16 interposed therein and pump means in the form of an eductor-type or jet-type pump, generally designated by the numeral 18. The jet pump 18 includes a liquid jet nozzle orifice 20 formed therein which ejects a liquid flowstream into a cavity 22 and aimed at an orifice 24. The nozzle orifice 20 is typically slightly smaller than the orifice 24 and will induce a flow of fluid from branch cavity portions 23 and 25 of the cavity 22 to be entrained with the liquid flowstream leaving the jet pump by way of a conduit 28. This type of pump also provides for thorough mixing of vapor entering the cavity portions 23 and 25 with the liquid jet stream whereby a complete mixing of the fluids occurs in the pump 18 and in the conduit 28 so that the flowstream is normally an equilibrium condition between vapor and liquid.

The flowstream from the conduit 28 is preferably conducted to a combined centrifugal separator and vapor-liquid contacting means comprising a packed column 30 characterized by a generally cylindrical housing 31 forming a chamber 32 into which the conduit 28 opens in a tangential direction. The packed column 30 preferably includes means to facilitate vapor and liquid contact such as glass spheres or Raschig rings 34. The flowstream entering the column 30 permits the flow of liquid hydrocarbon to trickle down and exit the bottom of the column through a conduit 36 which may include a flowmeter 38 interposed therein. The conduit 36 empties into a reservoir 40 which is preferably maintained at atmospheric pressure as is the interior chamber 32 of the packed column 30. Liquid flowing into the reservoir 40 may be re-injected into the transmission line 10 by way of a pump 42 and conduit 44.

Vapor from the packed column 30 flows through a conduit 46 to a detection device 48 and which is in flow communication with the pump 18. The system 12 further includes a source 50 of the fluid whose concentration is to be determined with respect to the liquid flowing through the pipeline 10, which fluid may be hydrogen sulfide, for example. The source 50 is connected by way of a conduit 52 and flow control valve 54 to a vapor bubble counter 56 for determining the quantity of fluid to be measured which is being conducted to the pump 18 by way of a conduit 58.

The detector device 48 may be of a type commercially available and is preferably of a type which does not consume or alter the chemical composition of the gas being detected although, if a type of detector device 48 is used which is consumptive the flowrate of vapor or gas through the conduit 46 will require measurement. In this regard, a flowmeter such as the orifice flowmeter 47 may be interposed in the conduit 46. A preferred type of detector device for use in the system 12, for measuring the concentration of hydrogen sulfide in a liquid hydrocarbon stream, is a nonconsumptive type hydrogen sulfide detector for detecting the concentration of hydrogen sulfide in a vapor stream. For example, the detector device 48 may comprise a type manufactured by Bacharach, Inc., Pittsburg, Penna. under their designation System 130. This type of gas detector device may be mounted in such a way that the vapor flowing through the conduit 46 is exposed to a transducer unit of the gas detector in a chamber formed by a suitable vessel through which the vapor or gas flows and returns to the pump inlet chamber 25 by way of a conduit portion 49. The flow of gas from the gas liquid separator chamber 32 through the gas detector 48 is induced by the pump 18. If the gas detector 48 is of the nonconsumptive type then the gas or vapor flowrate through the conduit 46 is not required to be measured.

In accordance with the present invention, the concentration of a substance such as hydrogen sulfide in a hydrocarbon liquid flowstream can be determined by measuring the incremental indicated gas phase concentration of the substance to be measured. By providing a recirculating stream of vapor of the composition whose concentration in a liquid is to be determined, a recirculating stream of vapor can be measured to determine the incremental change in concentration of the substance to be measured in the vapor stream to determine the concentration of the substance in the liquid stream initially and which is in equilibrium with the measured vapor stream.

For example, in the operation of the system 12, the valve 16 may be controlled to permit flow of liquid from the transmission line 10 through the pump means 18 to initially establish an equilibrium condition between the vapor and the liquid in the chamber 32. The vapor will continuously flow through the conduit 46 and the gas detector 48 to the pump 18 as it is drawn into the pump by the eductor provided by the nozzle orifice 20 and the diffuser orifice 24. Care should be taken that the temperature and pressure in the chamber 32 is maintained substantially constant during the measurement process. Preferably, the chamber 32 is maintained at atmospheric pressure and liquid is returned to the transmission line at substantially the same rate as it is withdrawn. If the nozzle orifice 20 is approximately 0.0625 inches diameter and the diffuse orifice 24 is 0.078 inches diameter the pump 18 will pump approximately 1600 ml/minute of liquid at an inlet pressure to the pump of 30 psig and will pump approximately 900 ml/minute of vapor if the suction port pressures are maintained at about the same as the eductor or pump outlet pressure. The liquid and vapor leave the pump 18 together and mix thoroughly in the conduit 28, but are separated in the chamber 32 wherein the liquid and vapor are substantially at equilibrium conditions.

If the gas detector 48 is of the type referenced above, there is no need to measure the flow rate of vapor in the conduit 46 and a reading of the concentration of the composition to be measured, such as hydrogen sulfide, is taken. These readings can be arbitrary numbers since an incremental change in the reading of the gas detector 48 is used as the basis for determining the concentration of the composition to be measured in the liquid flow stream. Assume that the initial reading is 100 units. Now, if the source of a substance whose initial concentration is to be measured, such as hydrogen sulfide, is admitted to the pump 18 through the bubble counter 56 at a known rate, say a weight equivalent of ten parts per million based on the flow rate of the liquid flowstream, this rate is allowed to flow to the pump 18 until equilibrium conditions are reached in the conduit 28, the chamber 32, the conduit 46 and the gas detector 48.

At this point a second reading is established by the detector device 48, for example, a reading of 120 units, indicating an increase in the concentration of hydrogen sulfide gas in the recirculating vapor flowstream. If a reading of the gas detector device 48 indicates an incremental change of twenty units for ten parts per million then the gas detector device measures gas concentrations at the rate of two units per part per million and if the original reading was 100 units then the concentration of the fluid being measured in the liquid flowstream initially is 100 units divided by two units per part per million or 50 parts per million.

Accordingly, using the foregoing process and system, as described, the concentration of a substance such as hydrogen sulfide in a liquid such as a liquid hydrogen may be determined by measuring the concentration of the substance to be measured in a vapor flowstream which is in equilibrium with the liquid itself. Moreover. With the system and method described herein none of the substance to be measured leaves the system as a gas or vapor. Consequently, this type of detection method and system is advantageous for use with toxic substances such as hydrogen sulfide.

Those skilled in the art will recognize that the pump means 18 may be replaced by another type of pump which is capable of mixing a gas with the liquid flowstream from both the recirculating vapor stream and the source of a gas whose incremental change in the flowstream is to be measured. However, the eductor or jet type pump 18 is particularly advantageous in that it may be used to induce the flow of vapor through the recirculating circuit and from the substance source using the liquid being measured itself. Moreover, the eductor or jet type pump also promotes thorough mixing of the gas or vapor with the liquid to more readily establish the equilibrium condition in the chamber 32. Still further, the vapor recirculation system simplifies the calculation of the incremental change in liquid concentration of the substance to be measured caused by the addition of the calibrating vapor, which vapor leaves the system only when dissolved in liquid. This compares favorably with systems where the concentration of the substance to be measured in the liquid changes from the system inlet to outlet.

As previously mentioned, the gas detector device 48 may be of a type commercially available and the bubble counter 56 may also be of a type commercially available or merely, as shown, a closed glass tube or vessel 57 at least partially filled with a liquid and into which a gas discharge tube 59 projects whereby bubbles 61 of measured size and condition may be counted as the flow of gas through the device is controlled by the valve 54.

Although a preferred method and system of the present invention have been described in detail herein, those skilled in the art will recognize that various substitutions and modifications may be made to the invention without departing from the scope and spirit of the appended claims.

What is claimed is:

1. A method for determining the concentration of a gas substance in a liquid comprising the steps of:
    placing a flowstream of the liquid in equilibrium with a flowstream of vapor containing the gas to be measured and determining the concentration of the gas to be measured in said vapor flowstream;
    adding a quantity of the gas to be measured at a known rate to the liquid flowstream which is in equilibrium with said vapor flowstream and measuring the change in concentration in the vapor flowstream of the gas to be measured to determine the incremental change of concentration of the gas to be measured in the liquid flowstream for a known rate of gas added to said liquid flowstream; and
    dividing the measurement of the concentration of gas in the vapor flowstream which is in equilibrium with said liquid by the incremental unit increase in concentration of the gas in the vapor flowstream to determine the concentration of gas to be measured in the liquid flowstream initially.

2. The method set forth in claim 1 including the steps of:
    mixing the liquid flowstream with a recirculating vapor flowstream;
    separating the liquid flowstream from the vapor flowstream in a chamber wherein the liquid flowstream and the vapor flowstream are maintained in equilibrium.

3. The method set forth in claim 2 including the step of:
    withdrawing liquid from the chamber at substantially the same rate as it is added to the chamber.

4. The method set forth in claim 1 wherein:
    said liquid flowstream and said vapor flowstream are mixed in an eductor type pump utilizing the liquid flowstream as the pumping medium.

5. The method set forth in claim 4 wherein:
    a known quantity of gas is added to the liquid flowstream by said eductor type pump.

6. The method set forth in claim 4 including the step of:
    passing said quantity of gas added to said flowstream through flow measuring means to measure the flow rate of gas added to the liquid flowstream and recirculating vapor flowstream.

7. A system for measuring the concentration of a substance in a liquid, wherein said substance may be in gaseous form in equilibrium with said liquid at a particular concentration of said substance in said liquid, comprising:
    means for mixing a liquid flowstream with a vapor flowstream containing said substance;
    means for separating vapor from said liquid;
    means for circulating a vapor flowstream separated from said liquid and reintroducing said vapor flowstream to said liquid flowstream at said means for mixing;
    detection means interposed in said vapor flowstream for measuring the concentration of said substance in said vapor flowstream; and
    means for adding a known quantity of said substance to said liquid flowstream whereby the incremental change in the concentration of said substance in said vapor flowstream may be measured to determine the concentration of said substance in said liquid flowstream initially.

8. The system set forth in claim 7 wherein:
    said means for separating includes means for establishing an equilibrium condition between said liquid and said vapor at a predetermined pressure and temperature condition.

9. The system set forth in claim 8 wherein:
    said means for establishing said equilibrium condition comprises means forming a packed column.

10. The system set forth in claim 9 wherein:
    said packed column includes a chamber and said system includes means in communication with said chamber for collecting liquid separated from said vapor flowstream.

11. The system set forth in claim 7 wherein:
    said means for mixing said liquid with said vapor flowstream comprises pump means for pumping said vapor flowstream from said means for separating to conduit means for mixing with said liquid flowstream leading to said separator means whereby a vapor flowstream is mixed with and placed in equilibrium with said liquid in said means for separating.

12. The system set forth in claim 11 wherein:

said pump means comprises a jet type pump utilizing said liquid flowstream to induce flow of vapor from said means for separating to mix with a liquid flowstream being conducted to said means for separating.

13. The system set forth in claim 12 wherein:

said means for adding a known quantity of said substance to said liquid flowstream is connected to said jet type pump for inducing the flow of said substance from said source to mix with said liquid flowstream flowing through said jet type pump.

14. The system set forth in claim 7 wherein:

said means for detecting said substance in said vapor flowstream comprises a nonconsumptive gas detector for detecting the concentration of a gas comprising said substance in said vapor flowstream.

15. A system for measuring the concentration of a vapor dissolved in a liquid flowing through a pipeline and the like, wherein said vapor may be in equilibrium with said liquid at a particular concentration of said vapor in said liquid, comprising:

means for mixing a liquid flowstream withdrawn from said pipeline with a flowstream of said vapor;

means for separating vapor from said liquid;

means for circulating a flowstream of said vapor separated from said liquid and reintroducing said flowstream of said vapor to said liquid flowstream at said means for mixing;

detection means interposed in said flowstream of said vapor for measuring the concentration of said vapor in said flowstream of said vapor;

means for adding a known quantity of said vapor to said liquid flowstream whereby the incremental change in the concentration of said vapor in said flowstream of said vapor may be measured to determine the concentration of said vapor in said liquid flowstream initially; and means for returning liquid separated from said vapor to said pipeline and whereby substantially all of said vapor in said system that leaves system is dissolved in said liquid.

16. The system set forth in claim 15 wherein:

said means for separating includes means for establishing an equilibrium condition between said liquid and said vapor.

* * * * *